United States Patent
Slemon et al.

(10) Patent No.: US 6,703,504 B2
(45) Date of Patent: Mar. 9, 2004

(54) CONFORMATIONALLY CONSTRAINED COMPOUNDS AS DENDRIMER CORES

(75) Inventors: Clarke Slemon, 1260 Ave. Docteur Penfield, #206, Montreal, Quebec (CA), H3G 1B6; Bohumil Macel, Westmount (CA); Latchazar Trifonov, Quebec (CA); Jean Vaugeois, Verdun (CA)

(73) Assignee: Clarke Slemon, Potland (CA)

( * ) Notice: Subject to any disclaimer, the term of this patent is extended or adjusted under 35 U.S.C. 154(b) by 60 days.

(21) Appl. No.: 10/071,206

(22) Filed: Feb. 11, 2002

(65) Prior Publication Data

US 2003/0232932 A1 Dec. 18, 2003

(51) Int. Cl.$^7$ .................. C07D 239/00; C07D 221/18; C07D 235/00; C07C 41/00
(52) U.S. Cl. ............... 544/245; 546/26; 546/184; 548/301.7; 568/579; 568/585; 568/631; 568/633
(58) Field of Search .................. 544/245; 546/26, 546/184; 548/301.7; 568/579, 585, 586, 631, 633

(56) References Cited

FOREIGN PATENT DOCUMENTS

| JP | 07 179034 A | 7/1995 |
|---|---|---|
| WO | WO 01 49649 A | 7/2001 |

OTHER PUBLICATIONS

Patent Abstracts of Japan, vol. 1995, No. 10, Nov. 30, 1995.
Clark W M et al.: "A Highly Enantioselective Conjugate Reduction of 3–Arylinden–1–Ones Using Baker's Yeast of the Preparation of (S)–3–Arylindan–1–Ones", Organic Letters, American Chemical Society U.S., vol. 1, No.11, 1999, pp. 1839–1842.
S. Wawzonek et al.: "The action of sulfuric acid ethyl 3,3–diphenyl–3–hydroxypropanoate", Journal of Organic Chemistry, vol. 36, 1971, pp. 1116–1121.
Weintraub J G et al: "Synthesis and chiroptical properties of amphiphilic dendrimers based on 2,3–dihydroxybenzyl alcohol", Tetrahendron, Elsevier Science Publishers, Amsterdam, NL, vol. 57, No. 46, Nov. 12, 2001, pp. 9393–9402.
Weintraub, Jacob G., et al., *Synthesis and Chiroptical Properties of Amphiphilic Dendrimers based on 2,3–dihydroxybenzyl Alcohol*, Sep. 19, 2001, pp. 9393–9402, Tetrahedron 57.
Takarabe, Kunihide and Kunitake, Toyoki, *Stopped–Flow/Rapid–Quenching Study of the Reaction of 1,1–Diphenylethylene and $CF_3SO_3H$*, 1980, pp. 239–244, Polymer Journal, vol. 12, No. 4.

Brown, Herbert C. and Okamoto, Y., *Electrophilic Substituent Constants*, Sep. 20, 1958, pp. 4979–4987.
Fischer, Marco and Vögtle, Fritz, *Dendrimers: From Design to Application—A Progress Report*, 1999, pp. 885–905, Angew. Chem. Int. Ed. 38.
Cacchi, Sandro and LUPI, Alessandro, *Palladium–Catalysed Hydroxycarbonylation of Vinyl and Aryl Triflates: Synthesis of $\alpha,\beta$–Unsaturated and Aromatic Carboxylic Acids*, 1992, pp. 3939–3942, Tetrahedron Letters, vol. 33, No. 27, Great Britain.
Rohde, Jason M. and Parquette, Jon R., *Synthesis of Dendrimers Containing 2,5–Anhydro–D–mannitol as a Chiral, Tetrafunctional Central Core with $C_2$ Symmetry*, 1989, pp. 9161–9164, Tetrahedron Letters, vol. 39.
Recker, Janosch, et al., *Folding Dendrons: The Development of Solvent–, Temperature–, and Generation–Dependent Chiral Conformational Order in Intramolecularly Hydrogen–Bonded Dendrons*, 2000, pp. 10298–10307, J. American Chemical Society, United States of America.
Bosman, A.W., et al., *About Dendrimers: Structure, Physical Properties, and Applications*, 1999, pp. 1665–1688, Chemical Review.
Dubber, Michael and Lindhorst, Thisbe K., *Synthesis of chiral carbohydrate–centered dendrimers*, 1998, pp. 1265–1266, Chem. Commun.
Rossi, Roberto A. and Bunnett, J.F., *A General Conversion of Phenols to Anilines*, 1972, p. 3570, J. Org. Chem, vol. 37, No. 19, 4A.
Tomalia, Donald A., et al., *Starburst Dendrimers: Molecular–Level Control of Size, Shape, Surface Chemistry, Topology, and Flexibility from Atoms to Macroscopic Matter*, 1990, pp. 138–175, Angew. Chem. Int. Ed. Engl. 29.

Primary Examiner—Shailendra Kumar
Assistant Examiner—Sikarl A. Witherspoon
(74) Attorney, Agent, or Firm—Ridout & Maybee LLP (57) ABSTRACT

There are provided novel chemical compounds and their uses in the preparation of polymers and oligomers, and the preparation of such compounds. In certain embodiments there are provided dendritic polymers and oligomers, of a type having at least four polymeric or oligomeric organic chains emanating from a single chemical core, each of the chains being of substantially equal length and substantially the same chemical composition. Such compounds may be referred to as dendrimers. Also provided are novel chemical entities useful as core entities in the preparation of dentrimers. Dendrimers can recognize a core substructure to which the polymeric/oligomeric chains ("dendrons") are covalenty attached and from which they extend with systematic branching radially outward in a three dimensional fashion, to approximately the same extent to each other. Together, core and dendrons constitute macromolecules possessing a high degree of internal structural replication attributable to the branches.

20 Claims, 6 Drawing Sheets

CONFORMATIONALLY CONSTRAINED COMPOUNDS AS DENDRIMER CORES

FIELD OF THE INVENTION

This invention relates to novel chemical compounds and their uses in the preparation of polymers and oligomers, and the preparation of such compounds. It also relates to polymers and oligomers prepared using such compounds, and processes for the preparation of the polymers and oligomers. More particularly, this invention relates to dendritic polymers and oligomers, of the type having at least four polymeric or oligomeric organic chains emanating from a single chemical core, each of the chains being of substantially equal length and substantially the same chemical composition. Such dendritic polymers and oligomers are referred to herein, for convenience, as dendrimers.

BACKGROUND OF THE INVENTION AND PRIOR ART

Dendrimers as defined above are known chemical entities. Practitioners of the chemical arts of dendrimers can recognize a core substructure to which the polymeric/oligomeric chains ("dendrons") are covalently attached and from which they extend with systematic branching radially outward in a three dimensional fashion, to approximately the same extent as each other. Together, core and dendrons constitute macromolecules possessing a high degree of internal structural replication attributable to the branches. The symmetry, partial symmetry or asymmetry of the dendrimer is a partial reflection of the impact of the core. Because of the influence of both core and branches, the chemical end groups of the chains are disposed on the surface of the macromolecules. All together, core, dendrons and surface functionalities determine the properties of the polymer. Accordingly a wide variety of such materials can be prepared with different but predetermined size and shape characteristics and different but predetermined chemical surface characteristics, useful in a variety of different practical applications (chromatographic supports, catalytic supports, synthetic membranes, for example). A review of dendrimers of this type, their preparation, properties, characteristics and uses, is found in *Angew. Chem. Int. Ed. Engl.* (1990), 29, 138, authored by Tomalia, Donald A., Naylor, Adel M., and Goddard III, William A. The disclosure of that review is incorporated herein in its entirety.

An important feature in determining the final characteristics of such a dendrimer is the choice of core chemical entity and its properties. Some of these properties have been noted in the prior art, others have not. Among the various properties which such a core entity could beneficially possess are:

a high degree of conformational rigidity, so that each dendron may start from a point in space more or less specifically defined with respect to the starting points of other dendrons. The shape, in three dimensional space of the polyhedron, defined by the starting positions of the functional groups from which the dendrons eventually protrude, is in this way a characteristic property of a core. If the dendrons are flexible but the dendrimer is to have some substantial element of controlled shape, that shape is largely dictated by the rigid core;

a large number of identical functionalities to which the dendrons may be attached. This will reduce the number of generations before the dendrimer surface assumes an essential spherical shape covered by a large number of surface reactive groups;

core functionalities sterically well separated, to reduce the likelihood of intramolecular branch defects; and an overall low symmetry and chirality, so that in cases where the dendrimer is to be used in a natural biological environment, the dendrimer will more closely mimic such environment.

Many different compounds have been proposed in the prior art, for use as the core entity of such dendrimers. The aforementioned article of Tomalia et. al. discloses ammonia, amines, linear polyethyleneimines, polyethylene glycols and a number of others. More complex cores, including chiral cores, have also been used. The range of possible candidates is very broad. Jason M. Rohde and Jon R. Parquette, in "Synthesis of dendrimers containing 2,5-anhydro-D-mannitol as chiral tetra-functional central core with C2 symmetry", *Tetrahedron Letters* (1998), 39, 9161 disclose the use of 1,3,4,6-tetra-O-(4-hydroxybenzoyl)-2,5-anhydro-D-mannitol as core for a dendrimer. Whilst an advance over small molecular cores, this compound still exhibits too much rotatidnal flexibility in its bonds and is thus capable of assuming too many conformations. The desirability of providing more rigid dendrimer cores, to obtain more extensive conformational order in the polymers, has recently been acknowledged by Weintraub et. al. in "Synthesis and chiroptical properties of amphiphilic dendrimers based on 2,3-dihydroxybenzyl alcohol", *Tetrahedron* (2001), 57, 9393.

SUMMARY OF THE INVENTION

It is an object of the present invention to provide novel chemical entities useful as core entities in the preparation of dendrimers.

It is a further object of the invention to provide novel dendrimers based on the novel chemical entities.

The present invention, from one aspect provides novel chemical entities useful as core entities in dendrimers and corresponding to the following general chemical structure Q.

Wherein:

at least one of the W and $W^1$ groups on a given phenyl ring is independently an electron-donating functionality and the other is independently selected from hydrogen and a bond of a fused rigid mono or polycyclic carbocyclic or N-heterocyclic ring involving either Z or an adjacent substituent R;

Z is either hydrogen or together with an adjacent substituent W or $W^1$, forms a fused rigid ring as aforesaid;

$R^1$ and $R^2$ are independently selected from hydrogen, a non-interfering chemical group, and a bond of a fused rigid mono or polycyclic carbocyclic or N-heterocyclic ring involving an adjacent substituent W on the same phenyl ring; or together represent a first bridge joining the respective carbon atoms to which each $R^1$ and $R^2$ is attached, said first bridge being selected from direct bond and —(CH$_2$)—;

T-butyl, chloro, bromo, iodo, alkylthio, halogen substituted methyl, lower alkoxy substituted methyl, lower alkylthio substituted methyl.

$R^3$ is selected from hydrogen, a non-interfering chemical group and a bond of a fused rigid mono or polycyclic carbocyclic or N-heterocyclic ring involving an adjacent substituent $W^1$, or $R^3$ forms a second bridge with $R^4$, said bridge joining the respective carbon atoms to which each $R^3$ and $R^4$ is attached and said second bridge being selected from direct bond, —(C═O)—, —(CH$_2$)— and —(CHOH)—;

$R^4$ is either hydrogen or together with $R^3$, forms the aforesaid second bridge, with the proviso that $R^1$ and $R^2$ do not form a bridge when $R^3$ and $R^4$ form a bridge;

$R^5$ is either hydrogen or together with $R^6$ forms a third bridge, said bridge joining the respective carbon atoms to which each $R^5$ and $R^6$ is attached and said third bridge being selected from, —(C═O), —(CH$_2$)— and —(CHOH)—;

$R^6$ is selected from hydrogen, a non-interfering chemical group and a bond of a fused rigid mono or polycyclic carbocyclic or N-heterocyclic ring involving an adjacent substituent $W^1$, or together with $R^5$ forms the aforesaid third bridge;

$R^7$ is selected from hydrogen, a non-interfering chemical group and a bond of a fused rigid mono or polycyclic carbocyclic or N-heterocyclic ring involving an adjacent substituent $W^1$;

$R^8$ is selected from hydrogen, a non-interfering chemical group and a bond of a fused rigid mono or polycyclic carbocyclic or N-heterocyclic ring involving an adjacent substituent W; and $R^9$ is selected from hydrogen, a non-interfering chemical group and a bond of a fused rigid mono or polycyclic carbocyclic or N-heterocyclic ring involving an adjacent substituent $W^1$.

Such a chemical entity provides a number of features, which in combination lead to the formation of highly desirable dendrimers based thereon. One such feature is the substantial orientational rigidity of aromatic rings with respect to the central indane (benzocyclopentane) moiety. The indane system is itself capable of no internal rotation and only slight flexing. Each aryl substituent on the five membered ring can effectively only rotate around that axis established by the specific carbon-carbon bond linking it directly to the central carbocycle.

The term "electron donating functionality" is used in this specification with more quantitative distinction than is the common understanding. This quantitative designation is based on the scale of specialized Hammett constants called $\sigma_p^+$ values established by Herbert C. Brown and Y. Okamoto in "Electrophilic Substitution Constants", *J. Am. Chem. Soc.*, (1958), 80, 4979. By the term, "electron donating functionality" as the term is used herein is meant a group having $\sigma_p^+<0$. Speaking qualitatively, such substituents activate their parent rings towards electrophilic aromatic substitution and direct this substitution to positions ortho and para to themselves, often with a significant preference for para substitution. They prominently activate and accelerate the electrophilic aromatic substitution of their parent rings.

Preferred electron-donating groups are hydroxyl, methoxyl, lower alkoxyl, nitrogen substituted lower alkoxyl, carboxyl substituted lower alkoxyl, acylated amino and sufonyl substituted amino.

"Non-interfering substituents" as the term is used herein means those that interfere neither with the course of chemical synthesis of the core molecules, nor in the course of the chain extension to prepare dendrimers from the core molecules. The choice of groups W or $W^1$ affects whether a particular group should be regarded as a non-interfering substituent. As a general guide, when W or $W^1$ has a $\sigma_p^+$ value of from about 0.0 to −0.5, a non-interfering substituent is one which has $\sigma_p^+>+0.2$. When W or $W^1$ has $\sigma_p^+<-0.5$, a non-interfering substituent is one which has $\sigma_p^+>-0.3$.

Fused rigid mono or polycyclic carbocyclic or N-heterocyclic rings are those chemical ring systems which contribute to the rigidity of the resulting core entity according to the invention. Preferred ring systems are ring systems which are essentially rigid with any attached substituents being essentially rigid and with no geometric or chiral centres introduced by the fusion of the two particular carbons of the ring system and the exactly corresponding two particular ring carbons of Q. Examples include aromatic monocyclic or polycyclic rings such as naphthyls, anthracyls, phenanthryls or the like; alicyclic rings such as cyclobutyls, cyclopentyls or cyclohexyls; N-heterocyclic rings such as pyridyl, piperidyl, imidazolyl or the like; the heterocyclic group should be chosen so as not to interfere with the subsequent use of the core entities in the dendrimer formation or the ease of chemical preparation of the core entities themselves. Sulfur or oxygen heterocycles are generally unsuitable. Preferred such fused rings are aromatic rings on account of their rigidity.

Another aspect of the invention is novel chemical compounds which can be reacted to form the dendrimer core entities according to the invention, namely indenone compounds of the general formula:

wherein:

W represents an electron-donating functionality; and

X and Y are different from one another and represent hydrogen or an electron-donating functionality, optionally, each of the other positions on the phenyl rings are substituted with non-interfering chemical groups.

A further aspect of the invention is a dendrimer comprising the core entity according to the invention, and organic chains outwardly emanating from said core entity. Dendrimers have self-limiting growth characteristics. The defect level becomes progressively higher and divergence from branch ideality becomes substantial at least by generation nine. The preferred dendrimers produced from cores of the invention are monodisperse, with branching ideality of 95% or greater, and with between zero and nine repetitions of the monomeric branching motif. In preferred embodiments of this aspect, the organic chains can be selected from the group consisting of:

O—[CH₂—C₆H₃-2,3-(CH₂—C₆H₃-2,3-[CH₂—C₆H₃-2,
   3-(CH₂—C₆H₄-4-COOH)₂]₂)₂],
O—[CH₂—C₆H₃-3,5-(CH₂—C₆H₃-3,5-[CH₂—C₆H₃-3,
   5-(CH₂—C₆H₄-4-COOH)₂]₂)₂],
O—[CH₂CH₂N(CH₂CH₂CONH CH₂CH₂N
   [CH₂CH₂CONHCH₂CH₂NH₂]₂)₂],
O—[CH₂CONHCH₂CH₂N(CH₂CH₂CONHCH₂CH₂N
   [CH₂CH₂CONH—CH₂CH₂NH₂]₂)₂],
O—[CH₂CH₂N(CH₂CH₂CONHCH₂CH₂N
   [CH₂CH₂CONH CH₂CH₂N(CH₂CH₂CO—
   NHCH₂CH₂NH₂)₂]₂)₂], and
O—[CH₂CONHCH₂CH₂N(CH₂CH₂CONHCH₂CH₂N
   [CH₂CH₂CONH—CH₂CH₂N
   (CH₂CH₂CONHCH₂CH₂NH₂)₂]₂)₂].

In more preferred embodiments, the organic chains may be of substantially equal length or of substantially the same chemical composition.

"Lower alkyls" as the term is used in this specification designates alkyls from $C_1$ to $C_6$.

BRIEF REFERENCE TO THE DRAWINGS

DESCRIPTION OF THE PREFERRED EMBODIMENTS

Preferred compounds for forming the core entity of a dendrimer according to the present invention have additional rigidity built into their chemical structures. This can be achieved by having additional structural constraints. For example, two of the aryl groups may be joined together by a further covalent bond, also, a suitable choice of R groups within the definition above can lead to compounds wherein the aryl groups are each prevented from rotating. Alternatively, or in addition, a phenyl group may be joined to the central indane by a further short covalent linkage, creating what is commonly known a fused ring, with the effect of freezing the conformation of the so-modified phenyl. There may be what is commonly known as a spiro attachment of one of the pendant phenyls onto the indanyl central ring system through bridging atoms. This Spiro fusion prevents the phenyl involved from rotating, and fixes all the attached functional groups to an exact position in space with respect to the central substructure.

Preferred choices of substituent functional groups W and $W^1$ are those, which have $\sigma_p^+$ values of less than −0.5. Examples of such groups include dimethylamino (−1.7), anilino (−1.4), amino (−1.3), hydroxy (−0.92) and methoxyl (−0.778). Also preferred are lower alkoxides, nitrogen substituted lower alkoxides, substituted amines, acylated amines, carboxyl substituted lower alkoxides and sulfonyl substituted amines. Additional functional groups with weaker activating effects and weaker directing effects can optionally be present on the phenyl rings of the molecules of the invention. It is specifically envisaged that some of these additional functional groups may serve to block specific positions on the phenyls and lead to improved yields of particular isomers in the course of synthesis. It is further specifically envisaged that some of these additional functional groups, may, having blocked certain positions and favoured certain isomers during synthesis, be simply replaced by hydrogen to give improved access to isomers of the compounds in which the additional functional groups are missing. For example, compound D of FIG. 5 might be formed from the dimerization of bis-1,1-(2-bromo-5-methoxyphenyl)ethene, and compound F might be formed after debromination of compound D. Compound F prepared in this way would have a different disposition of methoxy groups on the phenyl ring, than the major product of material prepared from bis-1,1-(3-methoxyphenyl)ethene.

The general structure Q allows that each of the main substituent functional groups W or $W^1$ is separated by at least one path of exactly five bond lengths from C-2 of the central five membered ring. This provides for greater symmetry in the final dendrimer, with polymeric chains of substantially equal length constituting the dendrons and all thereby extended substantially the same distance from a point on the core, for predetermined and symmetrical presentation of functional or other surface groups.

Figure 1:
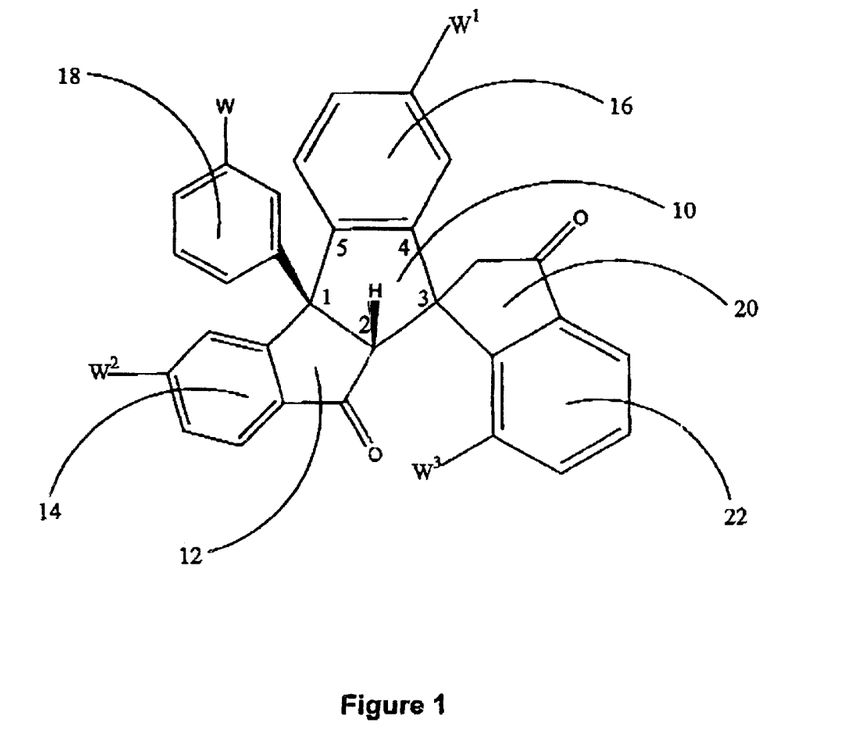
FIG. 1 of the accompanying drawings is the chemical structural formula of a preferred chemical entity of the present invention.

FIG. 1 of the accompanying drawings illustrates a preferred chemical entity according to the present invention. Each group W represents a strongly ortho-para directing group, and preferably represents the same group, e.g. OH. The central ring 10 is a five-membered carbocycle. Fused to the 1-2 bond thereof is an indanone system 12, the benzene ring 14 of which carries functional group $W^2$ at its meta position relative to its point of attachment to C-1. Fused to the 4-5 bond of a central ring 10 is a benzene ring 16, carrying a functional substituent $W^1$ at the position meta to C4. Covalently bonded to C-1 of the central five-membered ring is a phenyl ring 18 carrying a functional substituent W at a position meta to the connecting covalent bond. Attached in spiro fashion sharing C-3 of ring 10 is an indanone ring system 20, the benzene ring 22 of which carries functional substituent $W^3$ at its meta position with respect to its point of direct covalent bonding to ring 10; $W^3$ is also para to the ketone in ring system 20. The benzene ring 22 and the indanone system 12 may be disposed either in a cis or trans fashion on the central ring 10. It will be noted that all functional groups W are disposed four bond lengths or with four intervening carbon atoms (by at least one path) from a common point namely carbon 2 of the central ring 10. This provides for a high degree of symmetrical growth of a dendrimer from these four functional sites. Non-interfering substituents can be present at any or all of the available substitutable sites on the ring structure illustrated in FIG. 1, without departing from the scope of the invention.

The presence of carbonyl groups in the products of the present invention, as illustrated, is preferred but is not essential. Products containing carbonyl groups are relatively easy to synthesize, as described below. The carbonyl groups can be removed, however, by standard chemical methods (e.g. treatment of the compound of FIG. 1 by hydrogenolysis) and useful products obtained. The carbonyls can also be converted usefully to other functional groups. The above mentioned Tomalia et. al. publication refers at page 148 to "the inclusion of chromophores, chelating groups, metal, molecular recognition moieties, or hydrophobic/hydrophilic domains for desired guest host properties." The carbonyls provide a means to introduce such functional characteristics.

The chemical entity illustrated in FIG. 1 is one of a number of isomeric forms, all of which are within the scope of the invention. Separation of the various isomeric forms can be conducted on these compounds, by routine physico-chemical methods e.g. fractional crystallization. In order to improve the homogeneity of the final dendrimers made from these chemical entities as core products, it is in many instances desirable to conduct separation of the isomers from mixtures thereof, and to use only a single isomer as core entity for dendrimer formation. Some synthetic processes lead to the formation of a mixture of isomers, as described below, and separation of the isomers from one another, as well as from impurities in the reaction product mixture, is desirable.

Figure 2A:
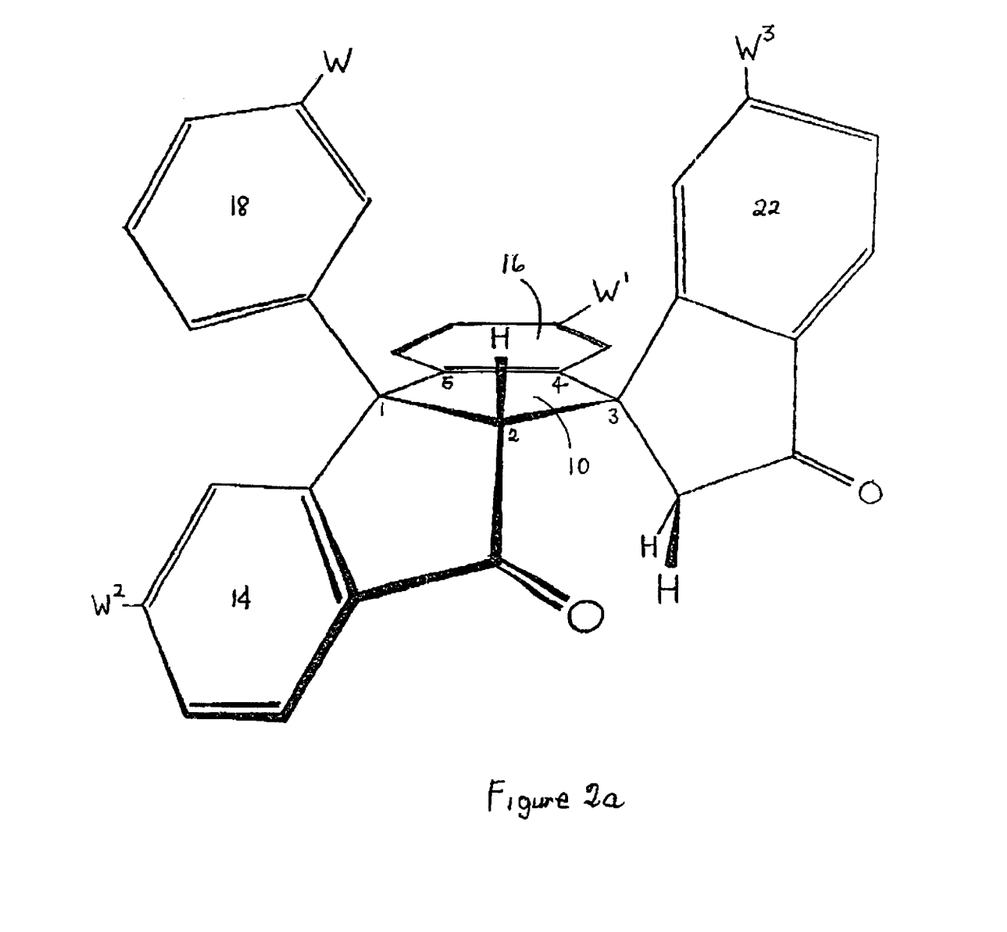
FIGS. 2a and 2b of the accompanying drawings are representations of the three-dimensional chemical structures of useful isomeric forms of the preferred chemical entity of FIG. 1.
Figure 2B:
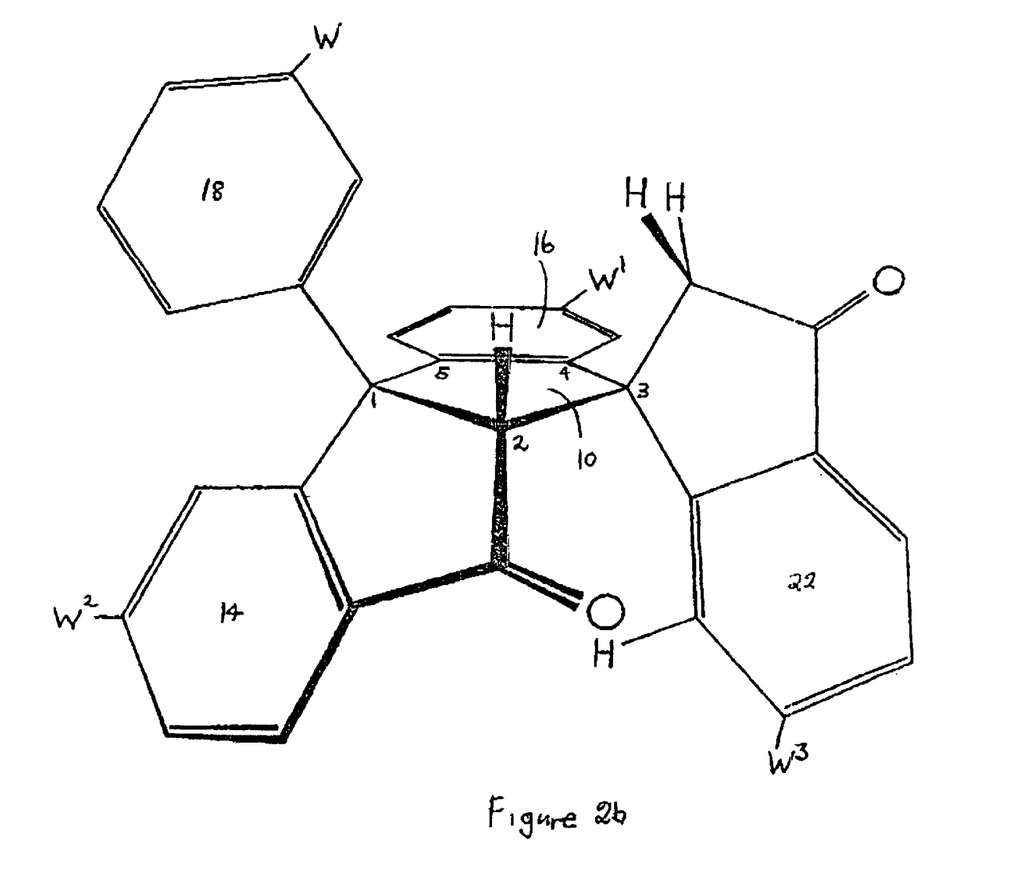

FIGS. 2a and 2b illustrate three-dimensionally two possible isomers of the compound of FIG. 1. It will firstly be noted that central ring 10 and fused ring 16 lie in a common plane (perpendicular to that of the paper) in both isomers, and this is a common, fixed feature of these compounds, of significance in their use as the core of a substantially symmetrical dendrimer. In the isomer of FIG. 2a, phenyl 22 is disposed trans to fused ring system 12, whereas in the isomer of FIG. 2b, the relative disposition is cis. In both cases, however, the functional groups W are all substantially equidistant from the 2-carbon of central ring 10. Since the functional groups in the two different isomers extend spatially in different directions in each case, however, it is preferred to use only one such isomer as the core of a dendrimer, for greater homogeneity of the resulting dendrimer product. It is a particular advantage of the present invention that isomers such as those shown in FIGS. 2a and 2b are readily separated from one another.

The compounds meeting the definition of structure Q or the compounds illustrated in FIGS. 1 and 2 can be synthesized generally according to methods known in the art, but with certain modifications. For example, 1,1-diphenyl ethylene has been transformed in the presence of a large number of various acids to 3-methyl-1,1,3-triphenyl indane (see Kunohife Takarabe and Toyoki Kunitake, *Polymer Science* (1980), 12(4), 239). A structure according to the present invention, 5-methoxy-1,1,3-tris-(3-methoxyphenyl)-3-methyl-indane, can be made in essentially quantitative yield from the cyclization-dimerization of bis-1,1-(3-methoxyphenyl)ethylene. This compound is then easily totally demethylated by treatment with boron tribromide to give 5-hydroxy-1,1,3-tris(3-hydroxyphenyl)ethylene an excellent dendrimer core. More interestingly, either the former compound or the latter compound can be further constrained by phenolic coupling between two of the rings to give compounds such as B of FIG. 5.

In another preferred embodiment, aryl rings are prevented from freely rotating by linking them by new rings to the central ring. These systems can be synthesized easily. One such synthetic method is based on the methods of Wawzonek, S. and Randen, N. A. in "The Action of Sulfuric Acid on Ethyl 3,3-Diphenyl-3-hydroxypropanoate", *J. Org. Chem.*, (1971), 36(8), 1116. This publication reports that treatment with sulfuric acid causes ethyl 3,3-diphenyl-3-hydroxypropanoate to yield isomeric ketones, namely trans and cis-spiro[indan-1-one-3,10'-[4b,9a]dihydro-4b-phenylindeno[1,2-a]inden-9-one, of formulae 2a and 2b, where the Ws are H. These compounds are unsubstituted versions of the compounds of the present invention. In accordance with either aspect of the present invention, the reaction reported by Wawzonek and Randen can be conducted using starting materials with appropriate substituents on the phenyl groups, i.e. ethyl 3,3-bis-(3'-methoxyphenyl)-3-hydroxypropanoate, to obtain compounds according to one embodiment of the invention, as a mixture of isomeric forms, from which the major isomer can be separated by fractional crystallization and other isomers separated by chromatography.

With substrates containing strongly electron donating substituents according to the present invention, sulphuric acid treatment, as described in the literature, does yield some products but unwanted sulfonation of the aromatic rings substantially occurs; therefore, non-sulfonating reaction conditions are generally preferred.

Figure 3:
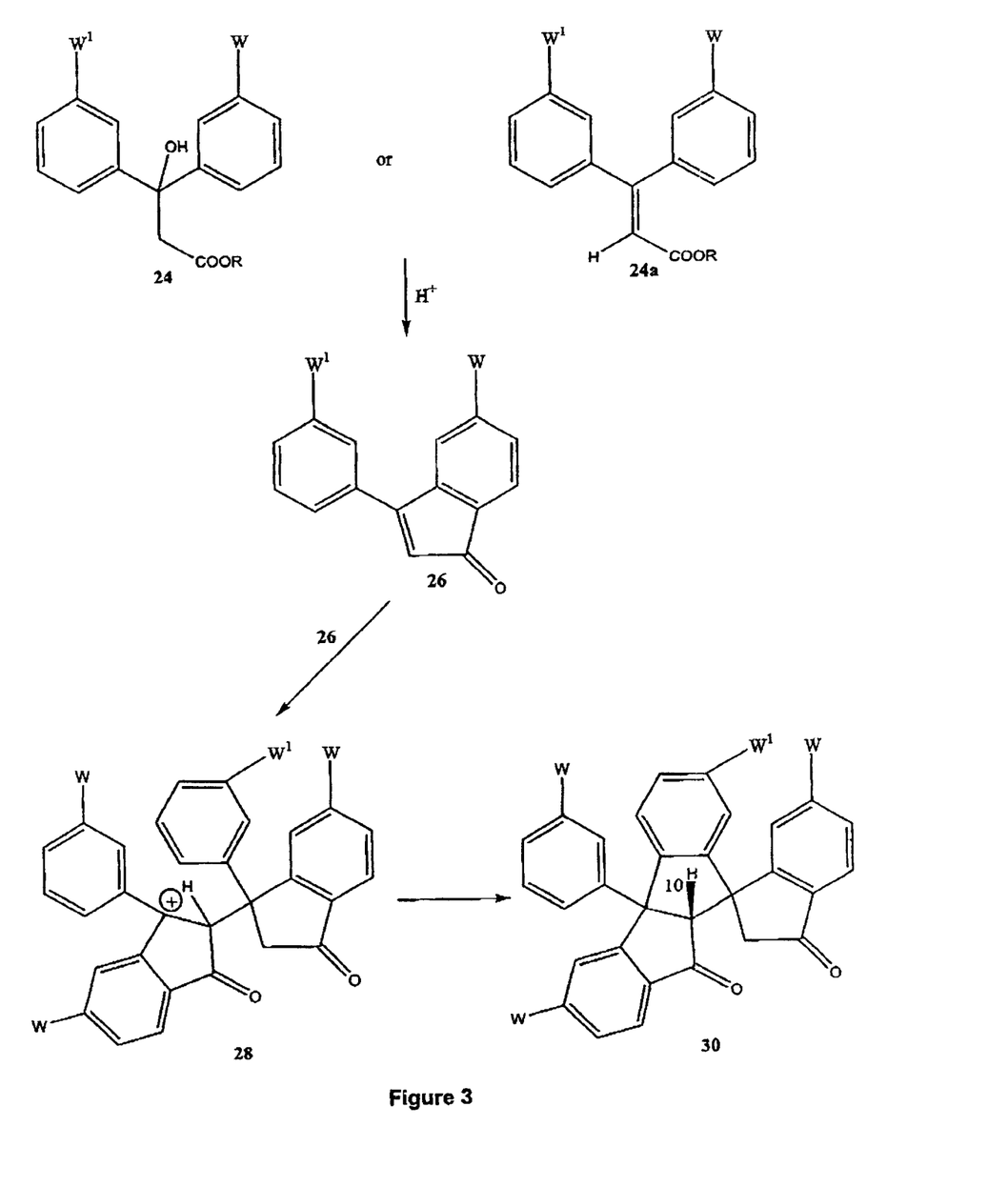
FIG. 3 is a representation of a chemical synthesis of the compound of FIG. 1.

An improved synthesis according to the invention, generally illustrated on FIG. 3 of the accompanying drawings, starts with a 3,3-(meta-substituted-phenyl) prop-2-enoate, compound 24a, or with a 3,3-(meta-substituted-phenyl)-3-hydroxypropanoate, compound 24; the substituents W an $W^1$ on the phenyl rings being strongly ortho- and para-directing groups. Reaction with strong acid of either the Bronsted or Lewis types, preferably methanesulfonic acid, triflic acid, trifluoroacetic acid, boron trifluoride etherate, boron trichloride, boron tribromide, titanium tetrachloride, or aluminum chloride causes this compound (either 24 or 24a) to cyclize to a substituted phenyl indenone 26. Th o-p directing effect of the W substituent directs the substitution on the phenyl ring at the position para to W, with some ortho substitution. It should be understood that the substitution can also occur on the other ring (ring bearing the $W^1$ substituent). In a preferred embodiment of the invention, the W substituents are the same on both phenyl rings.

Two indenones 26 then interact to couple together via the polarized double bond of the enone system, leading to an intermediate carbocation 28. This intermediate then undergo an intramolar cyclization to yield final compound 30, containing the central ring 10. In the cyclization of the intermediate 28, the strong o- and p-directing effect of the $W^1$ substituent dominates the orientation, causing a predominant intramolecular cyclization in the para position, with some ortho isomer. In a preferred embodiment of the reaction according to the invention, both rings in the starting material are identically substituted, therefore, only a single intermediate indenone is obtained regardless of which ring is involved in the cyclization.

Under the conditions of the reaction the intermediate carbocation behaves as if it were a diaryl substituted carbonium ion. It is important that this species should not be stabilized by electron donating aryl substituents. Strong ortho-para directing groups, which are disposed meta to this carbonium ion like site advantageously destabilize this species and make it highly reactive. A similar substituent on the remaining unfused aryl ring activates it to share electron density with this positive charge, forming the bond, which closes the indane system. The o- and p-directing substituents on the benzene rings ensure that the intended positions are involved in the cyclization reactions. In particular, substituent $W^1$ is key to the completion of the final cyclization step, forming central ring 10 by reaction at the para position of the benzene ring to which it is attached, to complete the fused ring structure, instead of polymerization of the intermediate molecule 26 as might occur with other types of substituents.

For particular choices of substituents, catalysts and reaction conditions, the indenones 26 are moderately stable isolable intermediates. Sometimes it is advantageous to purify these intermediates to remove minor amounts of ortho cyclization product and then submit the purified material to strong acid conditions sufficient to form the dimeric compounds of the invention. In this way, purer products can sometimes be obtained. These 3-(meta-substituted phenyl)-5 or 7-(substituted)-inden 1-ones can also be synthesized by the application of other methods known in the art, for preparing 2-unsubstituted 3-phenyl indenones.

The preparation of chiral cores is a preferred embodiment of the invention. Compounds of the trans and cis spiro [indan-1-one-3,10,-[4b,9a]dihydro-4b-phenylindeno[1,2-a] inden-9-one skeletal types can be resolved. This is done by using a sterically hindered hydride reducing agent in an appropriate stoichiometric amount to regioselectively and stereoselectively reduce one of the two ketones in the racemic starting material to give a racemic mixture of ketols. This alcohol mixture is tested with a panel of enzymes to determine which enzyme (or enzymes) selectively acylates just one of the ketol enantiomers. When the best enzyme has been determined, it is used to convert a synthetically useful amount of the ketol mixture to a mixture of chiral ketol and chiral keto-ester. These compounds can be separated by chromatography or by any other appropriate method for separating substances with significantly different physical properties. The other chiral ketol that was not acylated can be conveniently re-oxidized to yield one enantiomer of the original mixture. Hydrolysis of the keto-ester (obtained from enzymatic acylation) yields the other ketol enantiomer, which can be reoxidized to the other enantiomer.

The most preferred compounds of the present invention contain phenolic functions. These groups can be used to add dendrons directly using synthetic schemes already known in the art, or these phenols can be modified with short chain extensions that introduce another reactive functional group for dendron attachment. All these modifications simply apply reactions already known in the art for modifying phenols.

Particularly useful transformations are:
Ar—OH to Ar—O—CH$_2$COOR
Ar—OH to Ar—O—(CH$_2$)$_n$—N$_3$ and then to Ar—O—(CH$_2$)$_n$—NH$_2$
Ar—OH to Ar—O—CH$_2$—C$_6$H$_4$—COOR The same preferred phenolic functionalities can be subjected to reactions that replace the hydroxyl with another reactive functional group located at the same position on the carbocycle skeleton. These reactions are well known in the art and can readily be found by searching for transformations of phenols to another functional group in a reaction database on-line. A particularly useful reaction is the conversion of aryl triflates (readily available from the phenols) by transition metal catalyzed hydroxycarbonylation to carboxylic acids as in Sandro Cacchi, Alessandro Lupi, *Tetrahedron. Letters.* (1992), 33(27), 3939. Another reaction occasionally useful is the conversion of aryl diethyl phosphonates (directly available from phenols) to anilines by potassium amide in the presence of potassium metal catalysis in liquid ammonia as in Roberto A. Rossi and J. F. Bunnett, *J. Org. Chem.* (1972), 37(19), 3570. Transformations, which convert phenols to acid or basic functionalities, are particularly useful with regard to the practice of the invention because the products from such reactions are most amenable to simple purification and these functional groups are also simplest to use to start or connect dendrons.

The core entities of the present invention can be used to form dendrimers having a wide variety of dendrons or branch polymeric and oligomeric chains. Dendrimers can be synthesized by convergent addition of preformed dendrons to the core; by stepwise assembly of dendrons onto the core; or by some combination of these strategies. Chemical methods of formation of these are within the skill of the polymer and synthesis arts. They can be formed by addition polymerization of appropriate unsaturated monomers, or by condensation polymerization of bifunctional monomers, using conditions as to solvents, suspending media, catalysts, temperature etc. as known in the art. The dendrons can be linear or branched. In the embodiment shown in FIG. 4, branched amide oligomers, prepared by addition and condensation reactions, are shown, but this is purely for illustrative purposes.

Figure 4:
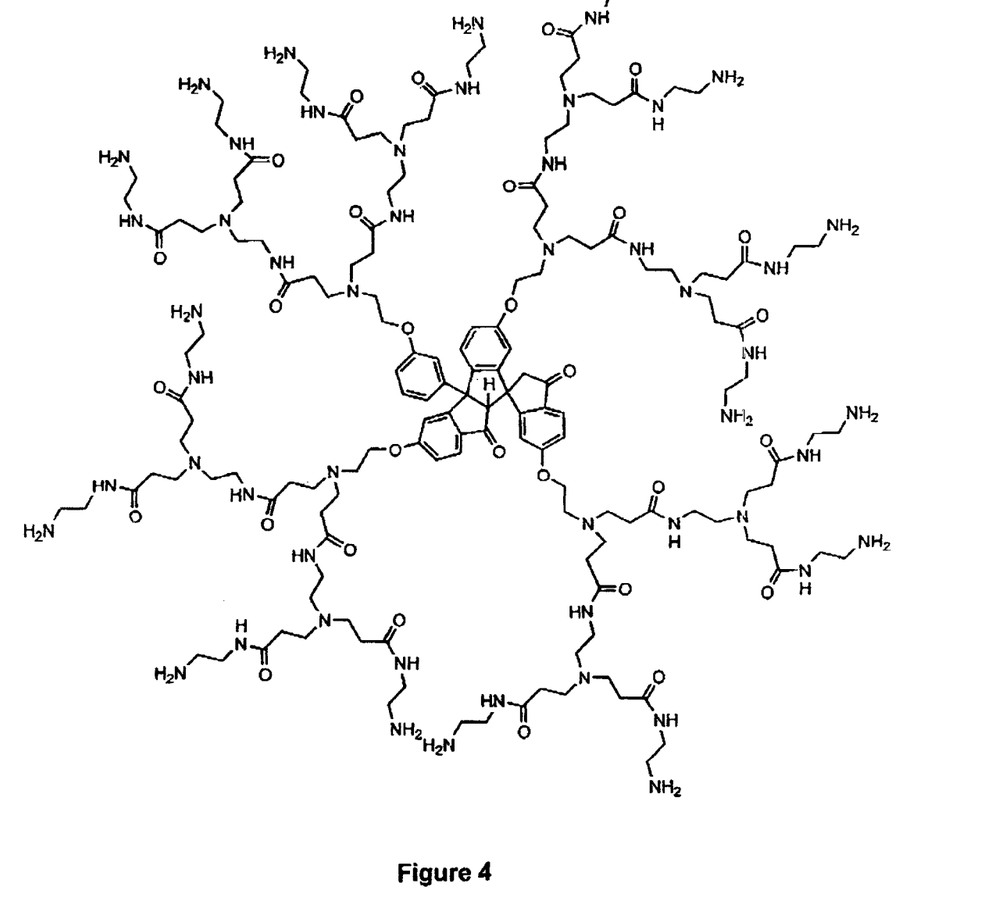
FIG. 4 of the accompanying drawings is an illustration of one embodiment of a dendrimer based the core chemical entity of FIG. 1.

In FIG. 4, a dendrimer of the invention has the core of FIG. 1 with W, W1, W2, W3 all —O—CH2CH2NH2 and the branching motif is [CH2CH2CONHCH2CH2N═]. It is present in zero and first generations in this example. In this example, there is no capping group. The chemical end groups are the free primary amino groups of generation 1 of the branching motif.

Figure 5:
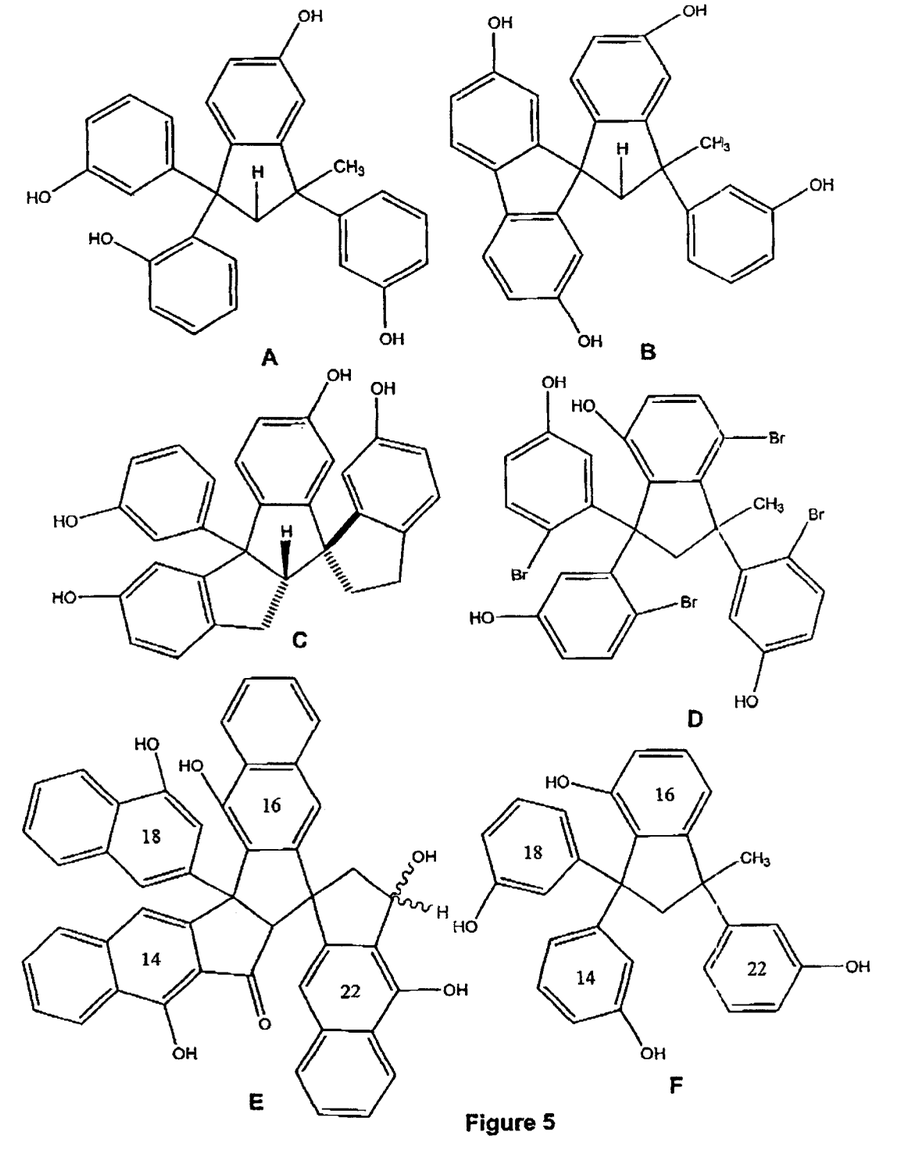
FIG. 5 shows chemical structural formulae of alternative chemical entities within the scope of the invention.

FIG. 5 of the accompanying drawings shows the chemical structure of various alternative compounds within the scope of the invention. Referencing back to general formula Q given above:

compound A of FIG. 5 is a dendrimer core according to the invention illustrated in general formula Q, wherein W group on each of rings 14, 18 and 22 as well as W$^1$ on ring 16 is hydroxyl and W$^1$ group on each of rings 14, 18 and 22 as well as W on ring 16 is hydrogen; each R group is hydrogen; and each Z group is hydrogen;

compound B of FIG. 5 is a dendrimer core according to the invention illustrated in general formula Q, wherein W$^1$ group on each of the phenyl rings is hydroxyl and W group on each of the phenyl rings is hydrogen; R$^1$ and R$^2$ form a direct bond and each of the other R groups is hydrogen; and each Z group is hydrogen;

compound C of FIG. 5 is a dendrimer core according to the invention illustrated in general formula Q, wherein W group on each of rings 14 and 18 as well as W$^1$ on each of rings 16 and 22 is hydroxyl, and W$^1$ group on each of ring 14 and 18 as well as W group on each of rings 16 and 22 is hydrogen; R$^3$ and R$^4$ form a —CH$_2$— bond, R$^5$ and R$^6$ also form a —CH$_2$— bond, and each of the other R groups is hydrogen; each Z group is hydrogen; and the stereochemistry of compound C is trans;

compound D of FIG. 5 is a dendrimer core according to the invention illustrated in general formula Q, wherein W group on each of rings 14, 16 and 22 as well as W$^1$ group on ring 18 is hydroxyl, and W$^1$ group on each of rings 14, 16 and 22 as well as W group on ring 18 is hydrogen; each of R$^1$, R$^3$, R$^6$, and R$^7$ groups is bromine and each of the other R groups is hydrogen; and each Z group is hydrogen;

compound E of FIG. 5 is a dendrimer core according to the invention illustrated in general formula Q, wherein W$^1$ group on each of rings 14, 18 and 22 as well as W group on ring 16 is hydroxyl, W group on each of rings 14, 18 and 22 as well as W$^1$ on ring 16 is involved in a further phenyl ring with an adjacent Z attached to the same phenyl ring; and R$^3$ and R$^4$ together form a —(C═O)— bridge, R$^5$ and R$^6$ together form a —(CHOH)— bridge, and each of the other R groups is hydrogen; and compound F of FIG. 5 is a dendrimer core according to the invention illustrated in general formula Q, wherein W group on each of rings 16 and 18 as well as W$^1$ group on each of rings 14 and 22 is hydroxyl, and W¹ group on each of rings 16 and 18 as well as W group on each of rings 14 and 22 is hydrogen; each of the R groups is hydrogen; and each of the Z groups is hydrogen.

It should be noted that all possible stereoisomers of each the dendrimer core entities as defined herein are within the scope of the invention.

The invention is further described, for illustrative purposes, in the following specific experimental examples.

SPECIFIC EXPERIMENTAL EXAMPLES

Synthesis of Ethyl 3,3-bis-(3-Methoxyphenyl)-3-hydroxypropionate

A 2000 mL three-necked, round-bottomed flask equipped with a magnetic stirring bar is the reaction vessel. The flask is furnished with, at one neck, a dry-ice cooled condenser with an oil bubbler on the vent, and at another neck a rubber septum with a bored hole connected with a length of a polyethylene tubing attaching it to an ammonia cylinder. The centre neck serves to charge the components and is temporarily plugged with a stopper. The interior of the flask is thoroughly flushed with nitrogen and the flask is immersed in an acetone-dry ice bath. Ammonia flow is passed into the flask until ca 500 mL of liquid is condensed, whereupon the flask is removed from the cooling bath. 2.84 g (0.41 gat) of lithium wire is cut into approximately 1 cm pieces and kept under hexanes. A small piece of this lithium is dropped into the flask, creating an intense ink-blue colour. Ca. 0.2 g of ferric nitrate nonohydrate is added. After the blue color is discharged, the rest of the lithium is added, piece by piece, blotting each piece with filter paper before the addition, and waiting after each addition until the transient blue color disappears. When addition is complete a light grey suspension is obtained. At this point, 36.1 g (0.41 mole) of ethyl acetate are added in a single portion via a syringe or dropping funnel. A dark solution is formed immediately. The solution mixture is stirred for about two minutes, quickly followed by addition of 49.6 g (0.205 mole) of 3,3'-dimethoxybenzophenone as a solution in 100 mL of diethyl ether. The reaction mixture is stirred for 30 minutes, then the reaction is quenched by adding 22 g (0.41 mole) of ammonium chloride. Additionally, 250 mL of ether are added and ammonia is allowed to evaporate, either on its own (overnight) or by gentle warming in a room temperature water bath. Water (150 mL) is added and the aqueous and ethereal phases are separated. The aqueous phase is further extracted twice with 100 mL portions of ether. The ethereal layers are all combined and washed with saturated brine. The ether is removed on a rotary evaporator. Ca. 68 g of brown, partially crystallizing, oil is obtained. The oil is subjected to distillation with steam, which removes some ethyl acetoacetate by-product. The remaing contents are cooled and the excess water carefully decanted. The solid residue is dissolved in ca. 200 mL of boiling ethanol, cooled, seeded (crystallizes slowly), and further cooled in an ice bath. The crystalline product is isolated by filtration, washed with a minimum of cold ethanol and dried in vacuum at 50° C. The yield is 69%, 47 g of beige product are obtained. ¹H NMR (CDCl₃): δ 7.3–6.7 (m, ArH, 8H), 5.1 (s, OH, 1H), 4.1 (q, $\underline{CH_2}$—CH₃, 2H), 3.75 (s, OCH₃, 6H), 3.25 (s, CH₂CO, 2H), 1.15 (t, CH₂$\underline{CH_3}$, 3H).

Synthesis of Ethyl 3,3-bis-(3-Hydroxyphenyl)-3-hydroxypropionate 22.4 g of 3,3'-dihydroxybenzophenone and 30 g hexamethyldisilazane are charged into a 100 mL single-neck flask equipped with a calcium chloride tube. The flask is immersed in an oil bath and the contents gradually heated to 150° C. When ammonia evolution ceased (ca. ½ hour), the flask contents are cooled to room temperature and transferred into a dropping funnel along with 100 mL of diethyl ether. Separately, ca. 250 mL of ammonia are condensed in a 1000 mL three-necked, round-bottomed flask and lithium amide slurry is prepared as in the above procedure for ethyl 3,3-bis-(3-methoxyphenyl)-3-hydroxypropionate, using 1.36 g of lithium. 17.26 g of ethyl acetate are rapidly injected from a syringe (in which it had been conveniently weighed). After about two minutes of stirring, the previously prepared silylated ketone is added and the resulting mixture stirred for 30 minutes. The mixture is quenched with 10.5 g of ammonium chloride. An additional 100 mL amount of ether are added and ammonia allowed to evaporate. 200 mL of water are added and when the inorganic salts dissolved, the pH is adjusted to pH 7 with citric acid. The layers are separated and the aqueous phase further extracted twice with 50 mL portions of ethyl acetate. The organics, all combined, are filtered through a Celite pad and the volatiles removed on a rotary evaporator. The resulting oil (24.2 g) is steam distilled to remove ethyl acetoacetate, and hexamethyidisiloxane by-products, as well as to quantitatively cleave any silyl groups still attached to the product. The product is taken up into ethyl acetate, dried over magnesium sulfate, and the solvent evaporated. By NMR analysis, this crude product is a mixture of the expected addition product (about 40–60 molar percent) and unreacted starting ketone. Most of the starting material can be removed by triturating with chloroform (100 mL) from which it alone crystallizes. The presence of the starting ketone, however, does not interfere in the subsequent cyclization-dimerization reaction. The yield after the treatment with chloroform is 41% theory, 13.1 g of brown oil are obtained. ¹H NMR (acetone-d6): 8.2 (bs, ArOH, 2H), 6.6–7.4 (m, ArH, 8H), 5.1 (s, OH, 1H), 4.05 (q, $\underline{CH_2}CH_3$, 2H), 3.2 (s, CH₂CO, 2H), 1.1 (t, CH₂$\underline{CH_3}$, 3H).

Synthesis of Racemic (1S,4'bS,9'aR)-4'b,9'a-Dihydro-4'b-(3"-hydroxyphenyl)-3',6,7'-trihydroxy-spiror[1H-indene-1,9'(10,H)indeno[1,2-a]indene]-3,10,(2H)-dione In this synthesis, methanesulfonic acid is used as solvent. 11 g of ethyl 3,3-bis-(3-hydroxyphenyl)-3-hydroxypropionate (containing ca. 50 mole % of 3,3'-dihydroxybenzophenone impurity, ca. 0.0213 mole of each) are dissolved in 50 mL of methanesulfonic acid and left at ambient temperature for 72 hours. A small sample is withdrawn, quenched in water, and the products extracted into ethyl acetate. The ethyl acetate layer is backwashed with saturated brine, dried with magnesium sulfate and analyzed by TLC (SiO₂ with fluorescent indicator; EtOAc:hexanes 7:3). The high $R_f$ spot corresponds to the unreacted 3,3'-dihydroxybenzophenone. The two principal low $R_f$ spots correspond to product isomers. The starting material (ethyl 3,3-bis(3-hydroxyphenyl)-3-hydroxypropionate) has essentially disappeared. The entire reaction mixture is quenched in ca. 300 mL of ice-water and the precipitated solids taken up in 100 mL of ethyl acetate. The ethyl acetate layer is separated, washed with saturated brine, dried over MgSO₄ and evaporated, yielding approximately 11 g of solid foam. This solid is redissolved in 60 mL of ethyl acetate, seeded (if applicable) with a small amount of previously obtained product and stirred at room temperature. Solid product comes out slowly and it is preferable to allow the crystallization take place over the course of several days (i.e. over the weekend). The solid is then filtered, washed with cold ethyl acetate, then ether, and dried in vacuum at ca 50° C. The yield is 25% of theory, about 1.28 g of essentially a single spot material is obtained. $^1$H NMR (acetone-d6): 9.5–8.0 (4×bs, OH, 4H), 7.6–5.7 (m, ArH, 13H), 3.44 (s, R$_3$CH, 1H), 3.08 (d, J=19 Hz, COCH$_2$, 1H), 2.98 (d, J=19 Hz, COCH$_2$, 1H).

Synthesis of Racemic (1S,4'bS,9'aR)-4'b,9'a-Dihydro-4'b-(3"-hydroxyphenyl)-3',6,7'-trihydroxy-spiro[1H-indene-1,9'(10,H)indeno[1,2-a]indene]-3,10,(2H)-dione In this synthesis boron trifluoride etherate is used as condensing reagent. 1 g of ethyl 3,3-bis-(3-hydroxyphenyl)-3-hydroxypropionate (containing ca. 30–40 mole % of 3,3'dihydroxybenzophenone) is dissolved in a minimal amount of ether (ca. 2 mL). 6 mL of boron trifluoride etherate are added via syringe. After 1 month at room temperature, the reaction mixture is quenched with water and the products taken up into ethyl acetate. The ethyl acetate phase is washed with water (2× to remove inorganic acids) and dried by passing the solution through a sodium sulfate plug. The solution is concentrated to a volume of ca. 5 mL and allowed to stand overnight. The deposited solid is filtered, washed with ethyl acetate and dried. NMR analysis shows the isomer identical with the samples obtained by cyclization-dimerization in protic acids. $^1$H NMR (acetone-d6): 9.5–8.0 (4×bs, OH, 4H), 7.6–5.7 (m, ArH, 13H), 3.44 (s, R$_3$CH, 1H), 3.08 (d, J=19 Hz, COCH$_2$, 1H), 2.98 (d, J=19 Hz, COCH$_2$, 1H).

Synthesis of Racemic (1R,4'bS,9'aR)-4'b,9'a-Dihydro-4'b-(3"-methoxyphenyl)-3',6,7'-trimethoxy-spiro[1H-indene-1,9'(10,H)indeno[1,2-a]indene]-3-ol-10,(2H)-one-cyclization-dimerization of Ethyl 3,3-bis-3-Methoxyphenyl)-3-hydroxypropionate 40 g of the title ester are dissolved in 200 mL anhydrous methanesulfonic acid and magnetically stirred. The solution, green at first, soon acquires a reddish-brown colour and ultimately turns dark red upon stirring overnight. A sample is withdrawn for TLC analysis. Workup: a few drops of the reaction mixture are quenched in water. The precipitated solid is taken up in ethyl acetate, washed with water, saturated sodium bicarbonate solution, dried over MgSO$_4$ and is ready for analysis. Plates: Silica gel G60 with fluorescent indicator. Mobile phase: ethyl acetate:hexanes 1:1. TLC analysis shows two dominant low R$_f$ spots (R$_f$=0.13 and R$_f$=0.31) corresponding to the isomeric products. There is no higher R$_f$ spot that would indicate presence of dehydrated ethyl 3,3-bis-(3-methoxyphenyl)-2-propenoate. This substance can be detected if a very early sample is taken. The whole batch is poured in a thin stream into ca. 500 mL of stirred ice water. The purplish solid is filtered and washed with water. It is resuspended in ca 500 mL of water; the pH adjusted to pH~7 with sodium hydroxide; filtered again; washed with water; and dried in vacuum at 50° C. The yield is ~100%, 33 g of purplish solid are obtained. The isomeric mixture is dissolved in 330 mL of boiling ethanol. Homogeneous brown solution formed at first starts depositing a white solid on continuous boiling. At this point, it is allowed to cool to room temperature and stirred overnight. The solid is isolated by filtration, washed with ethanol, ether and dried. Ca. 5–6 g of pure "cis" isomer (the higher of the two dominant spots on the TLC plate) are obtained. $^1$H NMR (CDCl$_3$): 7.8–5.8 (m, ArH, 13H), 3.9 (s, OMe, 3H) 3.8–3.6 (2×s, OMe, 6H), 3.55 (s, OMe, 3H), 3.45 (s, CH, 1H), 3.1 (d, J=18 Hz, 1H), 3.0 (d, J=18 Hz, 1H).

Synthesis of Racemic (1R,4'bS,9'aR)-4'b,9'a-Dihydro-4'b-(3"-methoxyphenyl)-3',6,7'-trimethoxy-spiro[1H-indene-1,9'(10,H)indeno[1,2-a]indene]-3-ol-10,(2H)-one 330 mg (1 mmole) of ethyl 3,3-bis-(3-methoxyphenyl)-3-hydroxypropionate are dissolved in 2 mL of methylene chloride. 1 mL (~7.8 mmoles) of boron trifluoride etherate is added via syringe. The solution turns dark red for an instant, then turns light red and starts turning gradually dark red afterwards. After three days at room temperature, the reaction mixture is quenched with water and methylene chloride-ether is removed on the rotary evaporator. The solid is filtered off, washed with water and dissolved in 5 mL of hot ethanol. The solution is allowed to stand for several days at room temperature after which time a beige solid is deposited. The solid is collected by filtration and triturated in fresh 5 mL of ethanol. The off white solid is filtered, washed with ethanol and dried. The yield is 37% theory, ca. 100 mg of the product are obtained. NMR analysis reveals "cis" isomer containing ca. 20 mole % of another "cis" isomer. More thorough purification can be achieved by dissolving the crude in small amount of methylene chloride, adding excess ethanol and distilling out methylene chloride. $^1$H NMR (CDCl$_3$): 7.8–5.8 (m, ArH, 13H), 3.9 (s, OMe, 3H) 3.8–3.6 (2×s, OMe, 6H), 3.55 (s, OMe, 3H), 3.45 (s, CH, 1H), 3.10 (d, J=18.5 Hz, 1H), 3.0 (d, J=18.5 Hz, 1H).

Synthesis of cis Racemic (S,4'bS,9'aR)-4'b,9'a-Dihydro-4'b-(3"-methoxyphenyl)-3',6,7'-trimethoxy-spiro[1H-indene-1,9'(10,H)indeno[1,2-a]indene]-3-ol-10,(2H)-one-methylation of Racemic cis-4'b,9'a-Dihydro-4'b-(3"-hydroxyphenyl)-3',6,7'-trihydroxy-spiro[1H-indene-1,9'(10,H)indeno]1,2-a]indene]-3,10,(2H)-dione 0.2523 g of "cis" racemic (1S,4'bS,9'aR)-4'b,9'a-dihydro-4'b-(3"-hydroxyphenyl)-3',6,7'-trihydroxy-spiro[1H-indene-1,9'(10,H)indeno[1,2-a]indene]-3,10,(2H)-dione (0.5 mmole) is dissolved in 1 mL of EtOH. To this solution is added 0.31 g of dimethylsulfate (2.46 mmole) followed by 0.104 g of NaOH (2.6 mmole) in 0.5 mL of water. The solution is heated to reflux. A crystalline material comes out within a short period of time. After about 10–15 minutes of reflux the mixture is cooled to a room temperature diluted with 5 mL of water (more solid material comes out) filtered, washed with water and dried in high vacuum at 50° C. The NMR spectrum of this product is identical with the spectrum of the major product obtained by direct cyclization—dimerization of ethyl 3,3-bis-(3-methoxyphenyl)-3-hydroxypropionate.

Synthesis of (±)(1R,4'bS,9'aR)-4'b,9'a-Dihydro-4'b-(3"-methoxyphenyl)-3',6,7'-trimethoxy-spiro[1H-indene-1,9'(10,H)indeno[1,2-a]indene]-3-ol-10,(2H)-one In a 25 mL round-bottomed flask equipped with a rubber septum, a magnetic stirring bar and a nitrogen inlet fitted with an oil bubbler, are dissolved 100 mg (0,19 mmole) of (±) (1S,4'bS,9'aR)-4'b,9'a-dihydro-4'b-(3"-methoxyphenyl) 3',6,7'-trimethoxy-spiro[1H-indene-1,9'(10,H)indeno[1,2-a] indene]-3,10,(2H)-dione in 10 mL of methylene chloride. The solution is cooled with an ice bath and 400 mL (0,4 mmole) of L-Selectride™ (1 mole*L$^{-1}$) in tetrahydrofuran are added. The mixture is stirred for 1 hour, then 500 mL of NaOH 5 mole*L$^{-1}$ are added, followed by ca. 500 mL of H$_2$O$_2$ 30%. The mixture is stirred vigorously for 10 minutes and 10 mL of water are added. The phases are separated. The organic phase is concentrated in vacuo and dried under 0,1 Torr at room temperature overnight, to give 95 mg (95%) of off-white solid identified as a single diastereomer of racemic (1R,4'bS,9'aR)-4'b,9'a-dihydro-4'b-(3"-methoxyphenyly)-3', 6,7'-trimethoxy-spiro[1H-indene-1,9'(10,H)indeno[1,2-a] indene]-3-ol-10,(2H)-one, from its characteristic signals at 2.57 ppm (d, J=15 Hz), 2.82 ppm (dd; J=7 Hz and 15 Hz) and 5.15 ppm (d, J=7 Hz) in the $^1$H NMR spectrum for the protons next to the carbinol and the carbinol proton respectively.

Resolution of Racemic (1R,4'bS,9'aR)-4'b,9'a-Dihydro-4'b-(3"-methoxyphenyl)-3',6,7'-trimethoxy-spiro[1H-indene-1,9'(10,H)indeno[1,2-a]indene]-3-ol-10,(2H)-one In a 25 mL round-bottomed flask equipped with a magnetic stirring bar and a stopper are suspended 50 mg of CHIROCLEC™ PC in 10 mL of t-butylmethyl ether containing one drop of water. To this solution are added 95 mg (0,18 mmole) of racemic (1R,4'bS,9'aR)-4'b,9'a-dihydro-4'b-(3"-methoxyphenyl)-3',6,7'-trimethoxy-spiro[1H-indene-1,9'(10,H)indeno[1,2-a]indene]-3-ol-10,(2H)-one, followed by 75 mL of vinyl acetate. The progress of the reaction is followed by HPLC. The reaction stops after 50% of the starting material is consumed. After 24 hours the suspension is filtered and the solvent is evaporated under vacuo. Analysis of the $^1$H NMR spectra of the residue shows a 1:1 mixture of the starting alcohol and its acetylated derivative. The residue is applied to 20×20 cm preparative thin-layer chromatographic plate of $SiO_2$ (2 mm) that is eluted twice with a 1:9 mixture of acetone and toluene. This treatment allows for the isolation of 46 mg of a trans-racemic (1R,4'bS,9'aS)-4'b,9'a-dihydro-4'b-(3"-methoxyphenyl)-3',6,7'-trimethoxy-spiro[1H-indene-1,9'(10,H)indeno[1,2-a]indene]-3-ol-10,(2H)-one whose R-(−)-α-methoxy-α-(trifluoromethyl)phenyl acetate derivative shows only one diastereomer by $^1$H NMR spectroscopy. (Characteristic doublets of 0.3 Hz at 6.05 ppm and 6.07 ppm can be seen in the $^1$H NMR spectrum of the diastereomeric mixture obtained from R-(−)-(α)-methoxy-α-(trifluoromethyl)phenyl acetyl chloride and the racemic mixture of alcohols).

Synthesis of Racemic (1R,4'bS,9'aR)-4'b,9'a-Dihydro-4'b-(3"-methoxyphenyl)-3',6,7'-trimethoxy-spiro[1H-indene-1,9'(10,H)indeno[1,2-a]indene]-3-ol-10,(2H)-one-demethylation of Racemic (1R,4'bS,9'aR)-4'b,9'a-Dihydro-4'b-(3"-methoxyphenyl)-3',6,7'-trimethoxy-spiro[1H-indene-1,9'(10,H)indeno[1,2-a]indene]-3-ol-10,(2H)-one 0.532 g (1 mmole) of the title tetramethoxy compound is dissolved in 5 mL of $CH_2Cl_2$. The solution is protected against moisture by a calcium chloride tube. The flask is cooled in a dry ice-acetone cooling bath whereupon a solution of 1.8 g (7.2 mmole) of $BBr_3$ in about 2 mL of $CH_2Cl_2$ is added slowly. The stirred solution is allowed to come to room temperature and is stirred for 20 hours. The solution is quenched in about 20 mL of ice water, saturated with salt and the product extracted into 15 mL of ethyl acetate. The organic layer is backwashed with saturated brine, dried over magnesium sulfate and volatiles removed on the rotatory evaporator. About 400 mg of the product are obtained. The NMR spectrum corresponds to the compound obtained directly from the cyclization-dimerization of ethyl 3,3-bis-(3-methoxyphenyl)-3-hydroxy-propionate. $^1$H NMR (DMSO-d6): 9.6–9 (4×bs, OH, 4H), 7.6–5.5 (m, ArH, 13H), 3.3 (s, $R_3$CH, 1H), 2.93 (s, $CH_2CO$, 2H).

Synthesis of 1,1-bis-(3-Methoxyphenyl)ethanol

A dry 100 mL three-necked, round-bottomed flask equipped with magnetic stirring, reflux condenser, nitrogen bubbler and thermometer is charged with 0.73 g (30 mgat) of magnesium shavings and ca. 1 mL of dry ether. 4.5 g (30 mmoles) of iodomethane as a solution in ca 5 mL of ether are placed in a pressure equilibrated dropping funnel. The funnel is mounted in the central neck of the flask. A small crystal of iodine is dropped in the flask followed by about 1 mL of the iodomethane solution. When the reaction starts, the rest of the iodomethane is added dropwise, so as to maintain a gentle reflux. When the addition is complete, the solution is refluxed for 15 minutes, then cooled in an ice bath. The dropping funnel is now charged with a solution of 4.85 g (20 mmoles) of 3,3'-dimethoxybenzophenone in 10 mL of ether. The ketone is added to the Grignard reagent solution dropwise or in small portions so that the reaction is not too violent. After addition of the ketone the resulting solution is refluxed briefly (15 minutes), then cooled to room temperature. The reaction is quenched by addition of 15 g of ice. The precipitated magnesium hydroxide is dissolved by addition of 2 g of citric acid. The different layers are separated, the lower aqueous layer is extracted with 5 mL of ether. Both ethereal extracts combined are washed consecutively with water and 10% sodium carbonate, dried over anh. $K_2CO_3$ and evaporated to yield 5.28 g (quant. based on benzophenone) of 1,1-bis-(3-methoxyphenyl)ethanol. $^1$H NMR ($CDCl_3$): 6.7–7.3 (m, ArH, 8H), 3.75 (s, OMe, 6H), ~2.2 (bs, OH, 1H), 1.9 (s, C—Me, 3H).

Synthesis of 1,1-bis-(3-Methoxyphenyl)ethene 5.28 g (20 mmoles) of 1,1-bis(3-methoxyphenyl)ethanol are dissolved in 30 mL of glacial acetic acid. A catalytical amount of iodine is added and the solution refluxed for about 5–15 minutes or until the dehydration is complete. The progress of the reaction is monitored by TLC on silica (5% EtOAc in hexanes). The burgundy red solution is diluted with water (100 mL) and the product extracted with ether (2–3 extractions with 10 mL portions). The combined ethereal extracts are washed consecutively with water (into which a spatula tip of sodium metabisulfite was added) and 10% sodium carbonate, dried over anh. $K_2CO_3$ and evaporated to yield 4.63 g (96%) of the title compound. $^1$H NMR ($CDCl_3$): 6.8–7.3 (m, ArH, 8H), 5.45(s, C=$CH_2$, 2H), 3.75 (s, $OCH_3$, 6H).

Synthesis of 1,1,3-tris(3-Methoxyphenyl)-3-methyl-5-hydroxyindane-dimerization-cyclization of 1,1-bis(3-Methoxyphenyl)ethene 1.2 g of the title compound was dissolved in 6 mL of methanesulfonic acid. An exothermic reaction starts and the colour turns red. Some semi-solid waxy material forms a separate phase. After ca. 1 hour a sample is withdrawn and tested by TLC ($SiO_2$, 5% EtOAc in hexanes). If a complete absence of starting material is confirmed the whole reaction mixture is quenched with cold water, product extracted with ether, washed with 10% sodium carbonate, dried over anh. $K_2CO_3$ and the solvent is evaporated. The yield is ~100%, 1.16 g of 1,1,3-tris-(3-methoxyphenyl)-3-methyl-5-methoxyindane is obtained as a colourless oil. $^1$H NMR ($CDCl_3$): 6.5–7.3 (m, ArH, 15H), 3.77 (s, $OCH_3$, 3H), 3.72 (s, $OCH_3$, 3H), 3.68 (s, $OCH_3$, 3H), 3.62 (s, $OCH_3$, 3H), 3.33 (d, J=14 Hz, $CH_2$, 1H), 3.05 (d, J=14 Hz, $CH_2$, 1H), 1.54 (s, $CH_3$, 3H).

Synthesis of 1,1,3-tris-(3-Hydroxyphenyl)-3-methyl-5-hydroxyindane 1.16 g of the title compound is dissolved is 5 mL of dichloromethane and the solution cooled in dry ice-acetone mixture. 2.42 g (0.913 mL) of boron tribromide are introduced via a syringe. The solution is allowed to come to room temperature. After three hours a sample is withdrawn, quenched in water, product extracted into ethyl acetate, dried and solvent evaporated. NMR analysis shows absence of the methoxy signals in the starting material. The whole reaction mixture is quenched in ice-water, product extracted into ethyl acetate, washed with water, dried over $MgSO_4$ and solvent evaporated to yield 1.08 g (quant.) of product 1,1,3-tris-(3-hydroxyphenyl3-methyl-5-hydroxyindane. $^1H$ NMR (acetone-d6): 8.19 (s, OH, 2H), 8.12 (s, OH, 1H), 8.06 (s, OH, 1H), 7.2–6.3 (m, ArH, 15H), 3.25 (d, J=13.5 Hz, $CH_2$, 1H), 3.025 (d, J=13.5 Hz, $CH_2$, 1H), 1.4 (s, $CH_3$, 3H).

We claim:

1. A chemical compound of the general formula:

wherein:
- at least one of the W and $W^1$ groups on a given phenyl ring is independently an electron-donating functionality and the other is independently selected from hydrogen and a bond of a fused rigid mono or polycyclic carbocyclic or N-heterocyclic ring involving either Z or an adjacent substituent R;
- Z is either hydrogen or together with an adjacent substituent W or $W^1$, forms a fused rigid ring as aforesaid;
- $R_1$ and $R^2$ are independently selected from hydrogen, a non-interfering chemical group, and a bond of a fused rigid mono or polycyclic carbocyclic or N-heterocyclic ring involving an adjacent substituent W on the same phenyl ring; or together represent a first bridge joining the respective carbon atoms to which each $R^1$ and $R^2$ is attached, said first bridge being selected from direct bond and —($CH_2$)—;
- $R^3$ is selected from hydrogen, a non-interfering chemical group and a bond of a fused rigid mono or polycyclic carbocyclic or N-heterocyclic ring involving an adjacent substituent $W^1$, or $R^3$ forms a second bridge with $R^4$, said bridge joining the respective carbon atoms to which each $R^3$ and $R^4$ is attached and said second bridge being selected from direct bond, —(C=O)—, —($CH_2$)— and —(CHOH)—;
- $R^4$ is either hydrogen or together with $R^3$, forms the aforesaid second bridge, with the proviso that $R^1$ and $R^2$ do not form a bridge when $R^3$ and $R^4$ form a bridge;
- $R^5$ is either hydrogen or together with $R^6$ forms a third bridge, said bridge joining the respective carbon atoms to which each $R^5$ and $R^6$ is attached and said third bridge being selected from —(C=O)—, —($CH_2$)— and —(CHOH)—;
- $R^6$ is selected from hydrogen, a non-interfering chemical group and a bond of a fused rigid mono or polycyclic carbocyclic or N-heterocyclic ring involving an adjacent substituent $W^1$, or together with $R^5$ forms the aforesaid third bridge;
- $R^7$ is selected from hydrogen, a non-interfering chemical group and a bond of a fused rigid mono or polycyclic carbocyclic or N-heterocyclic ring involving an adjacent substituent $W^1$;
- $R^8$ is selected from hydrogen, a non-interfering chemical group and a bond of a fused rigid mono or polycyclic carbocyclic or N-heterocyclic ring involving an adjacent substituent W; and
- $R^9$ is selected from hydrogen, a non-interfering chemical group and a bond of a fused rigid mono or polycyclic carbocyclic or N-heterocyclic ring involving an adjacent substituent $W^1$.

2. The compound as defined in claim 1, wherein said electron-donating functionality is selected from the group consisting of: hydroxyl, methoxyl, alkylamino, arylamino, anilino, amino, lower alkoxyls, nitrogen substituted lower alkoxyls, substituted amines, acylated amino, carboxyl substituted lower alkoxyls, and sulfonyl substituted amino.

3. The compound as defined in claim 1, wherein said non-interfering chemical group is selected from t-butyl, chloro, bromo, iodo, alkylthio, halogen substituted methyl, lower alkoxy substituted methyl and lower alkylthio substituted methyl.

4. The compound as defined in claim 1, wherein said fused rigid ring is selected from the group consisting of: naphthyl, anthracyl, phenanthryl, cyclohexyl, cyclopentyl, cyclobutyl, pyridyl, piperidyl, and imidazolyl.

5. The compound as defined in claim 4, wherein said fused rigid ring is an aromatic ring.

6. The compound as defined in claim 2, wherein said second bridge is selected from direct bond, —(C=O)—, —($CH_2$)— and —(CHOH)—.

7. The compound as defined in claim 2, wherein said second bridge is —(C=O)—.

8. The compound as defined in claim 2, wherein said third bridge is selected from —(C=O)—, —($CH_2$)— and —(CHOH)—.

9. The compound as defined in claim 2, wherein said third bridge is —(C=O)—.

10. The compound as defined in claim 2, wherein, said second and third bridges are each independently selected from —(C=O)—, —($CH_2$)— and —(CHOH)—.

11. The compound as defined in claim 2, wherein each of said second and third bridges is —(C=O)—.

12. The compound as defined in claim 11, wherein said compound is an enantiomerically pure compound.

13. The compound as defined in claim 11, wherein said compound is a trans stereoisomer.

14. The compound as defined in claim 1, wherein each of the groups W and $W_1$ is separated by at least one path of five bond lengths from $C_2$ of the central 5-membered ring.

15. A dendrimer comprising the core entity as defined in claim 1 and organic chains outwardly emanating from said core entity.

16. A dendrimer comprising the core entity as defined in claim 2 and organic chains outwardly emanating from said core entity.

17. The dendrimer according to claim 16, wherein said organic chains are of substantially equal length.

18. The dendrimer according to claim 16, wherein said organic chains are of substantially the same chemical composition.

19. The dendrimer according to claim 16, wherein said organic chains are selected from the group consisting of:
O—[$CH_2$—$C_6H_3$-2,3-($CH_2$—$C_6H_3$-2,3-[$CH_2$—$C_6H_3$-2,3-($CH_2$—$C_6H_4$-4-COOH$)_2]_2)_2]_2$], O—[CH$_2$—C$_6$H$_3$-3,5-(CH$_2$—C$_6$H$_3$-3,5-[CH$_2$—C$_6$H$_3$-3,5-(CH$_2$—C$_6$H$_4$-4-COOH)$_2$]$_2$)$_2$], O—[CH$_2$CH$_2$N(CH$_2$CH$_2$CONH CH$_2$CH$_2$N[CH$_2$CH$_2$CONHCH$_2$CH$_2$NH$_2$]$_2$)$_2$], O—[CH$_2$CONHCH$_2$CH$_2$N(CH$_2$CH$_2$CONHCH$_2$CH$_2$N[CH$_2$CH$_2$CONH—CH$_2$CH$_2$NH$_2$]$_2$)$_2$], O—[CH$_2$CH$_2$N(CH$_2$CH$_2$CONHCH$_2$CH$_2$N[CH$_2$CH$_2$CONH CH$_2$CH$_2$N(CH$_2$CH$_2$CO—NHCH$_2$CH$_2$NH$_2$)$_2$]$_2$)$_2$], and O—[CH$_2$CONHCH$_2$CH$_2$N(CH$_2$CH$_2$CONHCH$_2$CH$_2$N[CH$_2$CH$_2$CONH—CH$_2$CH$_2$N(CH$_2$CH$_2$CONHCH$_2$CH$_2$NH$_2$)$_2$]$_2$)$_2$].

20. The dendrimer as defined in claim 16, wherein said organic chains are mono dispersed, with a branching ideality of 95% or greater, and with between 0 and 9 repetitions or the monomeric branching motif of said organic chains.

* * * * *